United States Patent [19]

Weigert

[11] Patent Number: 4,820,884
[45] Date of Patent: Apr. 11, 1989

[54] DEFLUORINATION PROCESS USING ACTIVATED CARBON

[75] Inventor: Frank J. Weigert, Wilmington, Del.

[73] Assignee: E. I. Du Pont de Nemours and Company, Wilmington, Del.

[21] Appl. No.: 129,371

[22] Filed: Nov. 24, 1987

Related U.S. Application Data

[63] Continuation-in-part of Ser. No. 73,878, Jul. 13, 1987, abandoned, which is a continuation of Ser. No. 785,960, Oct. 10, 1985, abandoned.

[51] Int. Cl.$^4$ .................. C07C 17/24; C07C 21/18; C07C 21/24
[52] U.S. Cl. .................. 570/156; 570/130; 570/132; 570/136; 570/157
[58] Field of Search ................ 570/156, 157

[56] References Cited

U.S. PATENT DOCUMENTS

| Re. 23,425 | 10/1951 | Harmon | 260/648 |
| 2,709,182 | 5/1955 | Farlow | 260/653 |
| 2,709,192 | 5/1955 | Farlow | 260/653 |
| 3,192,274 | 6/1965 | Baranauckas | 260/653.5 |

OTHER PUBLICATIONS

Patrick, et al., *Chemistry and Industry*, 1557-1558 (1963).
Bidinosti, et al., *J. Am. Chem. Soc. 83, 3737-3743 (1961)*.
Bacicocchi, *The Chemistry of Halides, Pseudo-Halides and Azides*, (1983), Chapter 5 161-201.

*Primary Examiner*—J. E. Evans

[57] ABSTRACT

A method for preparing an unsaturated fluorocarbon by defluorinating a perfluoroalkane employing activated carbon.

10 Claims, No Drawings

DEFLUORINATION PROCESS USING ACTIVATED CARBON

This application is a continuation-in-part of application Ser. No. 073,878 filed July 13, 1987, now abandoned, which in turn is a continuation of application Ser. No. 785,960 filed Oct. 10, 1985, now abandoned.

BACKGROUND OF THE INVENTION

1. Field of the Invention

This invention concerns a method for defluorinating a perfluoroalkane to the corresponding more highly unsaturated fluorocarbon.

2. References

U.S. Pat. No. 3,192,274, issued to Baranauckas, et al., on June 29, 1965, discloses a process for removing nonterminal halogens from saturated perhalocarbons by heating the perhalocarbons over a carbon catalyst at a temperature between about 275° and 450° C. All of the disclosed perhalocarbons contain at least one chlorine atom.

Patrick, et al., *Chemistry and Industry*, 1557 and 1558 (1963), disclose that passage of certain perfluorodimethylcyclohexanes over unactivated granular carbon at 600° C. gave a complex mixture of products including defluorinated products such as decafluoro-p- and -m-xylene. They also disclose defluorination of such compounds over iron and nickel. The authors state that perfuoro-1,2-dimethylcyclohexane is normally defluorinated by passage over iron gauze at 450°-500° to give decafluoro-o-xylene.

U.S. Pat. No. 2,709,182, issued to Farlow on May 24, 1955, discloses preparation of tetrafluoroethylene by a process wherein a fluorocarbon of at least three carbons and of a melting point no higher than 25° C. is pyrolyzed by heating at a temperature of at least 1500° C. Pyrolysis by passing the fluorocarbon between carbon electrodes is specifically disclosed.

U.S. Pat. No. 2,709,192, issued to Farlow on May 24, 1955, discloses a process for preparing tetrafluoroethylene wherein carbon tetrafluoride or hexafluoroethane or a mixture of these, is contacted with carbon at a temperature of at least 1700° C. and the resultant reaction mixture is rapidly quenched.

U.S. Pat. No. Re. 23,425, issued to Harmon on Oct. 30, 1951, discloses a process for making completely halogenated polyfluorohydrocarbons comprising heating at a temperature of at least 125° C. a completely halogenated ethylene of the formula $CX_2=CX_2$, wherein X is halogen and at least 2 of the halogens are fluorine. The use of activated charcoal in the process is disclosed.

Bidinosti, et al., *J. Am. Chem. Soc.* 83, 3737-3743 (1961), disclose low pressure pyrolysis of chlorinated methanes and ethanes and of chlorofluoromethanes and chlorofluoroethanes over graphite to give, in some cases, dehalogenated products.

Baciocchi, in "The Chemistry of Halides, Pseudo-Halides and Azides", Patai and Rappoport editors, John Wiley & Sons, New York, 1983, Chapter 5, pages 161 to 201, has reviewed 1,2-dehalogenations and related reactions.

SUMMARY OF THE INVENTION

This invention provides a process for preparing a perfluoroalkene having at least six carbon atoms and at least one carbon-carbon double bond comprising contacting the corresponding perfluoroalkane having at least two adjacent tertiary carbon atoms to defluorinate the perfluoroalkane, thereby forming the perfluoroalkene having, respectively, at least one carbon-carbon double bond.

DETAILED DESCRIPTION OF THE INVENTION

The products of the invention, perfluoroalkenes having at least one carbon-carbon double bond, are useful as comonomers for preparation of fluorocarbon-containing polymers. The instant process represents an improvement in prior art processes for preparing perfluoroalkenes in that lower temperatures can be employed and expensive metals such as platinum are not required.

The starting materials for the process of the invention are perfluoroalkanes having at least six carbon atoms. Suitable perfluoroalkanes have at least two adjacent tertiary carbon atoms. By "tertiary carbon atom" is meant one to which one fluorine atom is attached, all other attached atoms being carbon. Preferred reactants are perfluoroalkanes containing 6 to 14 carbon atoms. When a perfluoroalkane having only two adjacent tertiary carbon atoms is employed as the reactant, a perfluoroalk(mono)ene is usually the initial product. Further defluorination of the perfluoroalk(mono)ene to a perfluoroalkadiene can be achieved by adjustment of the process conditions, including use of a longer contact time. If the starting perfluoroalkane has more than one set of requisite adjacent tertiary carbon atoms, then the product can have more than two double bonds.

Representative perfluoroalkanes suitable as starting materials for the process of this invention include:
Perfluoro-2,3-dimethylbutane,
Perfluorodecahydronaphthalene,
Perfluoro-1-methyldecahydronaphthalene,
Perfluorotetradecahydroanthracene,
Perfluorotetradecahydrophenanthrene,
Perfluoro-1,2-dimethylcyclobutane.
Other useful reactants will suggest themselves to those skilled in the art upon reading this disclosure.

By "activated carbon" is meant an amorphous carbon having high adsorptivity for gases, vapors, and colloidal solids. Such activated carbons are typically formed from the carbon-source by heating to about 800° to 900° C. with steam or carbon dioxide to confer upon the carbon a porous internal structure. Any of the well-known activated carbons can be used in the practice of this invention as well as any carbons activated according to the disclosure provided herein or any of the techniques known in the art to improve carbon adsorptivity. Commercially available activated carbons useful in the process of this invention include those sold under the following trademarks: Darco ™, Nuchar ™, Columbia SBV ™, Columbia MBV ™, Columbia MBQ ™, Columbia JXC ™, Columbia CXC ™, Calgon PCB ™, and Barnaby Cheny NB ™. The source, grade, or form of the activated carbon is not critical. However, it is preferred to use granules to facilitate use in tubular reactors. The size of the granules is not critical but it is preferred to employ granules having an average mesh size of about 1/25 to ¼ of the reactor diameter.

In the process of the invention the perfluoroalkane is contacted with activated carbon at a temperature of from about 300° to about 500° C., preferably from about 350° to 450° C.

The process of this invention can be carried out readily in liquid or gas phase using well-known chemical engineering practice, which includes continuous, semi-continuous, or batch operations. The process is conveniently carried out at atmospheric pressure, although either higher or lower pressures can be employed. The type of reactor vessel used is not critical so long as it is able to withstand the temperatures and pressures employed. Reactor vessels of stainless steel are typically used although other materials such as nickel-based corrosion resistant alloys, such as Hastelloy TM alloy and tantalum can be used. The activated carbon can be used in a fixed bed or a fluidized bed configuration.

Contact times can vary from fractions of a second to 2 hours or more. Contact time is not critical since appreciable defluorination occurs even with relatively short contact times. For example, in a continuous flow process, a contact time as short as about 0.1 sec can be employed. In a batch process, a contact time of about 2 hr or longer can be used. When a continuous flow process is employed, contact time is calculated using the following equation.

$$\text{Contact Time} = \frac{\text{Volume of Carbon (mL)}}{\text{Gas Flow Rates (mL/hr)}}$$

The invention is further illustrated by the following examples in which all parts and percentages are by weight and all degrees are Celsius unless otherwise noted. unless otherwise specified, the activated carbon employed in the examples comprised 12 to 30 mesh (2.00 mm–600 $\mu$m) granules having a surface area of over 1000 m$^2$/g (Calgon PCB TM) as determined by standard nitrogen adsorption methods.

EXAMPLE 1

Defluorination of Perfluoro-2,3-dimethylbutane

A liquid flow of 2 mL/hr of perfluoro-2,3-dimethylbutane and 5 mL/min of nitrogen was passed over a bed of 2.5 g of activated carbon at various temperatures. The carbon was contained in a 1 cm diameter $\times$ 10 cm long stainless steel reactor which was heated in a fluidized sand bath. Effluent from the hot reactor was transported directly to a gas chromatograph and analyzed in a 6.10 m $\times$ 0.32 cm (20 ft $\times \frac{1}{8}$ in) column of C$_9$ fluorocarbon acrylate on a diatomaceous earth support isothermally at 32°. In addition to a peak for starting material at 14.6 minutes, two product peaks were observed. A liquid sample was collected and analyzed by both fluorine nmr and GC/MS on a fluorosilicone capillary column and the products were assigned as perfluoro-2,3-dimethylbutene and perfluoro-2,3-dimethylbutadiene, the result of successive defluorinations of the starting perfluoroalkane and the intermediate perfluoroalkene. Table 1 summarizes the proportions of the two products as the temperature was raised from 300° to 400° and the flow rates varied. The samples were taken at regular intervals over a 2-hr period.

TABLE 1

| Defluorination of Perfluoro-2,3-dimethylbutane[1] | | | |
|---|---|---|---|
| Sample | Alkane | Olefin | Diene |
| 1 | 41 | 12 | 40 |
| 2 | 55 | 20 | 20 |
| 3 | 62 | 21 | 9 |
| 4 | 71 | 16 | 2 |

TABLE 1-continued

| Defluorination of Perfluoro-2,3-dimethylbutane[1] | | | |
|---|---|---|---|
| Sample | Alkane | Olefin | Diene |
| 5 | 79 | 13 | 1 |

[1]All numbers are area percent. The sum is not 100% because minor amounts of unidentified products were also formed.

EXAMPLE 3

Defluorination of Perfluorotetradecahydrophenanthrene

A mixture of 2 g of activated carbon and 1 mL of perfluorotetradecahydrophenanthrene, admixed with the corresponding anthracene derivative, was heated in a sealed vessel at 400° for 4 hr. The recovered carbon was extracted with chloroform, and a fluorine nmr spectrum was obtained on the extract. The spectrum was consistent with a product mixture of perfluorooctahydrophenanthrene and perfluorooctahydroanthracene in about a 1:1 molar ratio.

EXAMPLE 3

Defluorination of Perfluorodecahydronaphthalene

A 1 mL sample of a mixture of cis and trans isomers of perfluorodecahydronaphthalene was heated in a sealed vessel with 1 g of activated carbon at 450° for 2 hr. The fluorine nmr spectrum of the resulting defluorinated product indicated the presence of perfluoro-9-octalin.

EXAMPLE 4

Defluorination of Perfluoro-1-methyldecahydronaphthalene

In a flow reactor similar to the one employed in Example 1, a liquid flow of 1 mL/hr of perfluoro-1-methyldecahydronaphthalene and 5 mL/min of nitrogen was passed over 3 g of activated carbon at 400°. Liquid was collected for one hour and analyzed by both F-19 nmr and GC/MS. Still present were three isomers of the starting materials, C$_{11}$F$_{20}$. One peak with an empirical formula of C$_{11}$F$_{18}$ was seen, which by fluorine nmr had the double bond in the 9–10 position. Two isomers of C$_{11}$F$_{14}$ were seen, which by nmr were identified as perfluoro-1- and perfluoro-2-methyltetralin, present in 7 and 1 area percent, respectively.

EXAMPLE 5

Defluorination of Perfluorodecahydronaphthalene

This Example demonstrates the use of several different types of activated carbon for the defluorination reaction. In a flow reactor similar to that employed in Example 1, a liquid flow of 1 mL/hr of a mixture of cis- and trans-perfluorodecahydronaphthalenes and 5 mL/min of nitrogen was passed over a bed of a designated activated carbon at a temperature of 450°. Liquid was collected for about 0.5 hr, and the product was analyzed by GC/MS on a fluorosilicone capillary column. The product obtained was perfluoro-9-octalin. The results ae summarized in Table 2.

TABLE 2

| Perfluorodecahydronaphthalene Defluorination over Various Activated Carbons[1] | | | |
|---|---|---|---|
| | Recovered Starting Material | | Product |
| Carbon | Trans-Isomer | Cis-Isomer | 9-Octalin |
| None | 53 | 43 | 0 |

TABLE 2-continued

Perfluorodecahydronaphthalene Defluorination over Various Activated Carbons[1]

| Carbon | Recovered Starting Material | | Product |
|---|---|---|---|
| | Trans-Isomer | Cis-Isomer | 9-Octalin |
| Control (Graphite) | 55 | 41 | <1 |
| Control (Colloidal) Graphite[2] | 50 | 23 | 1 |
| Nuchar TM | 53 | 17 | 24 |
| Darco TM | 55 | 38 | 3.6 |
| 2:1 C/SiO$_2$ | 48 | 30 | 10 |

[1]All numbers are area percent.
[2]The high surface area colloidal graphite was a commercial sample (Acheson Aquadag TM) which was subsequently isolated by freezing, filtering, washing and drying.

CONTROLS A-G

A gaseous flow of 5 mL/min of perfluorobutane was passed over a bed of 5 g of 8-30 mesh (2.36 mm-600 μm) activated carbon pellets at various temperatures. The carbon was contained in a 1 cm in diameter by 10 cm in length Vycor TM glass reactor which was heated in a split-tube furnace. Effluent from the hot reactor was transported directly for analysis at room temperature to a gas chromatograph equipped with a 20 m capillary column of —OCH$_2$CF$_3$ derivatized silicone oil and a flame ionization detector. Retention times for perfluorobutane (1.42 min), perfluoro-cis-2-butene (1.45 min) and perfluoro-trans-2-butene (1.62 min) were determined using known standards. The results are summarized in the table below.

TABLE 3

| Control | Temp. (°C.) | Total Area | Relative Area (%) | |
|---|---|---|---|---|
| | | | Butane | t-2-Butene |
| A | 275 | 120 | 100 | 0 |
| B | 325 | 95 | 100 | 0 |
| C | 375 | 208 | 100 | 0 |
| D | 425 | 267 | 100 | 0 |
| E | 475 | 159 | 100 | 0 |
| F | 525 | 28 | 62 | 36 |
| G | 575 | 2 | 57 | 43 |

These controls show that the defluorination process of the prior art, e.g. Baranauckas, et al. patent, cannot be used to predict the reactions of perfluorocarbons. This patent requires the presence of a chlorine atom on one of the adjacent carbon atoms of the fluorocarbon. These experiments show that when a chlorine is not present, i.e. use of perfluorobutane instead of 2-chlorononafluorobutane, defluorination does not occur at all within the temperature range of 275° C. to 450° C. specified in the patent. And when temperatures above the range specified in the patent are used, degradation occurs to the extent that insignificant amounts of the butane and butene survive.

It is also clear from these controls that the process of the present invention requires a critical relationship of the elements in the perfluoroalkane, namely, the perfluoroalkane must contain at least two adjacent tertiary carbon atoms.

The embodiments of the invention in which an exclusive property or privilege is claimed are defined as follows:

1. A process for preparing an unsaturated aliphatic or cycloaliphatic perfluorocarbon having at least six carbon atoms and having at least one carbon-carbon double bond comprising contacting the corresponding perfluoroalkane or perfluorocycloalkane having at least two adjacent tertiary carbon atoms with activated carbon at a temperature of from about 300° to about 500° C. to defluorinate said perfluoroalkane or perfluorocycloalkane, thereby forming the corresponding unsaturated aliphatic or cycloaliphatic perfluorocarbonn having at least one carbon-carbon double bond.

2. A process according to claim 1 wherein the perfluoroalkane or perfluorocycloalkane has from 6 to 14 carbon atoms.

3. A process according to claim 2 wherein the perfluoroalkane is perfluoro-2,3-dimethylbutane.

4. A process according to claim 2 wherein the perfluorocycloalkane is perfluoro-1,2-dimethylcyclobutane.

5. A process according to claim 2 wherein the perfluorocycloalkane is perfluorodecahydronaphthalene.

6. A process according to claim 2 wherein the perfluorocycloalkane is perfluorotetradecahydroanthracene.

7. A process according to claim 2 wherein the perfluorocycloalkane is perfluoro-1-methyldecahydronaphthalene.

8. A process according to claim 2 wherein the perfluorocycloalkane is perfluorotetradecahydrophenanthrene.

9. A process according to claim 1 wherein the temperature is from about 350° to about 450° C.

10. A process according to claim 9 wherein the activated carbon is in the form of granules.

* * * * *